United States Patent
Ding

(10) Patent No.: US 9,993,583 B2
(45) Date of Patent: *Jun. 12, 2018

(54) HIGH-DENSITY LIPOPROTEIN COATED MEDICAL DEVICES AND METHODS OF TREATMENT USING THE DEVICES

(71) Applicant: Abbott Cardiovascular Systems Inc., Santa Clara, CA (US)

(72) Inventor: Ni Ding, San Jose, CA (US)

(73) Assignee: ADVANCED CARDIOVASCULAR SYSTEMS, INC., Santa Clara, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/636,818

(22) Filed: Mar. 3, 2015

(65) Prior Publication Data

US 2015/0174303 A1 Jun. 25, 2015

Related U.S. Application Data

(60) Continuation of application No. 13/102,791, filed on May 6, 2011, now Pat. No. 9,138,513, which is a division of application No. 11/027,822, filed on Dec. 29, 2004, now Pat. No. 7,959,659, which is a continuation-in-part of application No. 11/001,225, filed on Nov. 30, 2004, now abandoned.

(60) Provisional application No. 60/534,045, filed on Jan. 2, 2004.

(51) Int. Cl.
| | | |
|---|---|---|
| A61L 31/16 | (2006.01) | |
| A61F 2/82 | (2013.01) | |
| A61K 38/17 | (2006.01) | |
| A61L 31/10 | (2006.01) | |

(52) U.S. Cl.
CPC ............... *A61L 31/16* (2013.01); *A61F 2/82* (2013.01); *A61K 38/1709* (2013.01); *A61L 31/10* (2013.01); *A61L 2300/252* (2013.01); *A61L 2300/416* (2013.01)

(58) Field of Classification Search
None
See application file for complete search history.

(56) References Cited

U.S. PATENT DOCUMENTS

| | | | |
|---|---|---|---|
| 4,916,193 A | 4/1990 | Tang et al. | |
| 4,994,071 A | 2/1991 | MacGregor | |
| 5,049,132 A | 9/1991 | Shaffer et al. | |
| 5,092,877 A | 3/1992 | Pinchuk | |
| 5,163,952 A | 11/1992 | Froix | |
| 5,304,121 A | 4/1994 | Sahatjian | |
| 5,342,621 A | 8/1994 | Eury et al. | |
| 5,464,650 A | 11/1995 | Berg et al. | |
| 5,468,253 A | 11/1995 | Bezwada et al. | |
| 5,637,113 A | 6/1997 | Tartaglia et al. | |
| 5,670,161 A | 9/1997 | Healy et al. | |
| 5,674,192 A | 10/1997 | Sahatjian et al. | |
| 5,733,327 A | 3/1998 | Igaki et al. | |
| 5,746,223 A | 5/1998 | Williams | |
| 5,776,184 A | 7/1998 | Tuch | |
| 5,801,141 A | 9/1998 | Steber et al. | |
| 5,858,400 A | 1/1999 | Williams | |
| 5,861,387 A | 1/1999 | Labrie et al. | |
| 5,928,667 A | 7/1999 | Rosenblatt et al. | |
| 5,948,435 A | 9/1999 | Williams | |
| 6,037,323 A | 3/2000 | Dasseux et al. | |
| 6,046,166 A | 4/2000 | Dasseux et al. | |
| 6,079,416 A | 6/2000 | Williams | |
| 6,110,483 A | 8/2000 | Whitbourne et al. | |
| 6,117,911 A * | 9/2000 | Grainger ............... | A61K 31/275 514/648 |
| 6,153,252 A | 11/2000 | Hossainy et al. | |
| 6,156,727 A | 12/2000 | Garber et al. | |
| 6,171,609 B1 * | 1/2001 | Kunz ................... | A61K 9/0024 424/422 |
| 6,265,377 B1 | 4/2001 | Dasseux et al. | |
| 6,251,920 B1 * | 6/2001 | Grainger ............... | A61K 9/0024 514/319 |
| 6,287,285 B1 * | 9/2001 | Michal ................. | A61L 31/10 424/422 |
| 6,299,604 B1 * | 10/2001 | Ragheb ................ | A61L 29/085 604/265 |
| 6,335,029 B1 * | 1/2002 | Kamath ................ | A61L 27/34 424/422 |
| 6,367,479 B1 | 4/2002 | Williams | |
| 6,376,464 B1 | 4/2002 | Dasseux et al. | |
| 6,485,514 B1 | 11/2002 | Wrenn, Jr. | |
| 6,514,533 B1 | 2/2003 | Burke et al. | |
| 6,518,412 B1 | 2/2003 | Dasseux et al. | |
| 6,548,548 B2 | 4/2003 | Campbell et al. | |
| 6,573,239 B1 | 6/2003 | Dasseux et al. | |
| 6,585,995 B1 | 7/2003 | Hanson | |
| 6,602,854 B1 | 8/2003 | Dasseux et al. | |
| 6,649,362 B2 | 11/2003 | Gamble et al. | |
| 6,656,216 B1 | 12/2003 | Hossainy et al. | |
| 6,663,880 B1 | 12/2003 | Roorda et al. | |

(Continued)

FOREIGN PATENT DOCUMENTS

| | | |
|---|---|---|
| EP | 1 247 537 A1 | 10/2002 |
| WO | WO 03/026492 | 4/2003 |
| WO | WO 03/072159 | 9/2003 |
| WO | WO 2005/068020 | 7/2005 |
| WO | WO 05/097186 | 10/2005 |

OTHER PUBLICATIONS

Degertekin (Minerva Cardioangiologica 50(5), 405-418, 2002).*
Chiesa, Guilia et al., "Apolipoprotein A-I$_{Milano}$: current perspectives," Current Opinion in Lipidology, 14(2), 2003, 159-163.
"Electronically Controlled Drug Delivery", book, Edited by B. Berner and S.M. Dinh, 1998, 4 pages.

(Continued)

*Primary Examiner* — Karlheinz R. Skowronek
*Assistant Examiner* — Ronald T Niebauer
(74) *Attorney, Agent, or Firm* — Squire Patton Boggs (US) LLP

(57) ABSTRACT

Method are disclosed for local and systemic administration HDL, recombinant HDL or HDLm for the prevention, treatment, or amelioration of a vascular disorder, disease or occlusion such as restenosis or vulnerable plaque.

23 Claims, No Drawings

(56) References Cited

U.S. PATENT DOCUMENTS

| | | | |
|---|---|---|---|
| 6,692,759 B1 | 2/2004 | Wong et al. | |
| 6,787,141 B1* | 9/2004 | Melvin | C07K 7/08 |
| | | | 424/185.1 |
| 6,790,228 B2 | 9/2004 | Hossainy et al. | |
| 6,896,965 B1* | 5/2005 | Hossainy | A61L 27/34 |
| | | | 428/411.1 |
| 6,905,700 B2 | 6/2005 | Won et al. | |
| 6,916,788 B2 | 7/2005 | Seo et al. | |
| 6,930,111 B2 | 8/2005 | Ibrahim et al. | |
| 6,998,388 B1 | 2/2006 | Cockerill et al. | |
| 7,105,018 B1* | 9/2006 | Yip | A61F 2/90 |
| | | | 623/1.15 |
| 7,226,612 B2 | 6/2007 | Sohier et al. | |
| 7,378,106 B2 | 5/2008 | Hossainy et al. | |
| 7,758,881 B2 | 7/2010 | Dugan et al. | |
| 7,769,420 B2 | 8/2010 | Silver et al. | |
| 7,959,659 B2 | 6/2011 | Ding | |
| 8,007,775 B2 | 8/2011 | Hossainy et al. | |
| 8,114,968 B2 | 2/2012 | Devy et al. | |
| 8,357,391 B2 | 1/2013 | Pacetti et al. | |
| 8,551,512 B2 | 10/2013 | Hossainy et al. | |
| 8,778,014 B1 | 7/2014 | Dugan et al. | |
| 2001/0051166 A1 | 12/2001 | Luo et al. | |
| 2002/0037919 A1 | 3/2002 | Hunter et al. | |
| 2002/0133224 A1 | 9/2002 | Bajgar et al. | |
| 2003/0088307 A1 | 5/2003 | Shulze et al. | |
| 2003/0109442 A1 | 6/2003 | Bisgaier et al. | |
| 2003/0125800 A1 | 7/2003 | Shulze et al. | |
| 2003/0139800 A1 | 7/2003 | Campbell | |
| 2003/0144727 A1 | 7/2003 | Rosenthal et al. | |
| 2003/0191179 A1 | 10/2003 | Josh-Hangal et al. | |
| 2003/0216699 A1 | 11/2003 | Falotico | |
| 2004/0224001 A1* | 11/2004 | Pacetti | A61L 31/10 |
| | | | 424/423 |
| 2005/0019366 A1* | 1/2005 | Zeldis | A61K 31/415 |
| | | | 424/423 |
| 2005/0019404 A1 | 1/2005 | Sung et al. | |
| 2005/0025799 A1* | 2/2005 | Hossainy | A61L 31/10 |
| | | | 424/423 |
| 2005/0070996 A1 | 3/2005 | Dinh et al. | |
| 2005/0070997 A1 | 3/2005 | Thornton et al. | |
| 2005/0074544 A1 | 4/2005 | Pacetii et al. | |
| 2005/0074545 A1 | 4/2005 | Thomas | |
| 2005/0106204 A1* | 5/2005 | Hossainy | A61L 31/10 |
| | | | 424/423 |
| 2005/0112170 A1 | 5/2005 | Hossainy et al. | |
| 2005/0112172 A1* | 5/2005 | Pacetti | A61L 31/10 |
| | | | 424/423 |
| 2005/0142202 A1 | 6/2005 | Roorda et al. | |
| 2005/0143808 A1* | 6/2005 | Hossainy | A61F 2/06 |
| | | | 623/1.42 |
| 2005/0147647 A1* | 7/2005 | Glauser | A61L 31/10 |
| | | | 424/426 |
| 2005/0163818 A1 | 7/2005 | Sung et al. | |
| 2005/0186248 A1* | 8/2005 | Hossainy | A61L 31/10 |
| | | | 424/423 |
| 2005/0222671 A1 | 10/2005 | Schaeffer et al. | |
| 2005/0261764 A1 | 11/2005 | Pacetti et al. | |
| 2005/0266044 A1 | 12/2005 | Szardenings | |
| 2005/0282734 A1 | 12/2005 | Kadima et al. | |
| 2005/0283229 A1 | 12/2005 | Dugan et al. | |
| 2006/0020243 A1 | 1/2006 | Speck et al. | |
| 2006/0045901 A1 | 3/2006 | Weber | |
| 2006/0065193 A1 | 3/2006 | Pacetti et al. | |
| 2006/0122689 A1 | 6/2006 | Kocur et al. | |
| 2006/0135476 A1 | 6/2006 | Kutryk et al. | |
| 2006/0147489 A1 | 7/2006 | Shanley et al. | |
| 2006/0206149 A1 | 9/2006 | Yun | |
| 2007/0026035 A1 | 2/2007 | Burke et al. | |
| 2007/0065479 A1* | 3/2007 | Zhang | A61L 31/14 |
| | | | 424/423 |
| 2007/0083258 A1 | 4/2007 | Falotico et al. | |
| 2007/0244549 A1 | 10/2007 | Pathak | |
| 2008/0181927 A1 | 7/2008 | Zhao | |
| 2009/0203602 A1 | 8/2009 | Gelber et al. | |
| 2009/0287300 A1 | 11/2009 | Dave et al. | |
| 2010/0023108 A1 | 1/2010 | Toner et al. | |
| 2010/0030183 A1 | 2/2010 | Toner et al. | |
| 2010/0233236 A1 | 9/2010 | Zhao | |
| 2011/0160575 A1 | 6/2011 | Beyar et al. | |
| 2011/0184384 A1 | 7/2011 | Davalian et al. | |
| 2011/0212139 A1 | 9/2011 | Ding | |
| 2011/0275980 A1 | 11/2011 | Weber et al. | |
| 2012/0035150 A1 | 2/2012 | Gaweco et al. | |
| 2012/0122838 A1 | 5/2012 | Ren et al. | |
| 2012/0263759 A1 | 10/2012 | Hossainy et al. | |

OTHER PUBLICATIONS

Chiesa et al., "Recombinant apolipoprotein A-I $_{Milano}$: a novel agent for the induction of regression of atherosclerotic plaques", Annals of Med. 35(4): 267-273 (2003).

Chroni et al., "The Central Helices of ApoA-I Can Promote ATP-binding Cassette Transporter A1 (ABCA1)-mediated Lipid Efflux", The J. of Biol. Chem. vol. 278, No. 9, pp. 6719-6730, 2003.

Gorshkova et al., "Lipid-Free Structure and Stability of Apolipoprotein A-I: Probing the Central Region by Mutation", Biochemistry, vol. 41, No. 33, pp. 10529-10539 (2002).

HeartSite.com "PTCA or Angioplasty," https://web.archive.org/web/20020808133747/http://www.heartsite.com/html/ptca.html, 2002, pp. 1-3.

Hu et al, "Expression of the human extracellular domain of high density lipoprotein receptor in methylotropic yeast", Yi Chuan Xue Bao, Jan; 30(1), 1 pg. (2003).

International Search Report and Written Opinion for PCT/US2004/043869 filed Dec. 29, 2004, dated May 6, 2005, 15 pgs.

Khan et al., "Single-Dose Intravenous Infusion of ETC-642, a 22-Mar ApoA-1 Analogue and Phosphollpids Complex, Elevates HDL-C in Atherosclerosis Patients", Circulation vol. 108, No. 17, 2570, (2003).

Medtronic: "The Procedure: What to Expect—Getting a Stent," https://www.medtronic.com/patients/coronary-artery-disease/getting-therapy/balloon-angioplasty-and-stenting/surger/[May 22, 2014 , Sep. 22, 2010, pp. 1-3.

Nissen et al., "Effect of Recombinant ApoA-1 Milano on Coronary Atherosclerosis in Patients with Acute Coronary Syndromes", JAMA, vol. 290, No. 17, pp. 2292-2300, (2003).

Panagotopulos et al., "Bacterial expression and characterization of mature apolipoprotein A-1", Protein Expression and Purification 25, pp. 353-361 (2002).

Perry et al., "Local Delivery of Antibiotics via an Implantable Pump in the Treatment of Osteomyelitis", Clin. Orthop. 226: pp. 222-230 (1988).

Rensen et al., "Recombinant Lipoproteins: Lipoprotein-Like Lipid Particles for Drug Targeting", Advanced Drug Delivery Reviews, vol. 47, pp. 251-276, (2001).

Tailleux et al., "Apolipoprotein A-II, HDL metabolism and atherosclerosis", Atherosclerosis 164, 13 pgs. (2002).

Tian et al., "Structural and functional properties of apolipoprotein A-I mutants containing disulfide-linked cysteines at positions 124 or 232", Biochimica et Biophysica Acta 1599, pp. 56-64 (2002).

Von Birgelen et al., "Relation Between Progression and Regression of Atherosclerotic Left Main Coronary Artery Disease and Serum Cholesterol Levels as Assessed with Serial Long-Term (≥ 12 Month) Follow-Up Intravascular Ultrasound", Circulation, pp. 2757-2762 (2003).

Kolata, G., Study Finds New Drug Acts Quickly on Clogged Arteries (Nov. 4, 2003) published online http://source.quidant.com/gdt_new/Industry_News_Report/2003/week45/industry_news_1, printed Nov. 10, 2003.

* cited by examiner

HIGH-DENSITY LIPOPROTEIN COATED MEDICAL DEVICES AND METHODS OF TREATMENT USING THE DEVICES

CROSS-REFERENCE TO RELATED APPLICATIONS

This application is a continuation of U.S. patent application Ser. No. 13/102,791, filed on May 6, 2011, published on Sep. 1, 2011, as US 2011/0212139 A1, and issued on Sep. 22, 2015, as U.S. Pat. No. 9,138,513 B2, which is a division of U.S. patent application Ser. No. 11/027,822, filed on Dec. 29, 2004, and issued as U.S. Pat. No. 7,959,659 on Jun. 14, 2011, which is a continuation-in-part of U.S. patent application Ser. No. 11/001,225, filed on Nov. 30, 2004, which claims the benefit of U.S. Provisional application Ser. No. 60/534,045, filed on Jan. 2, 2004. The teachings of U.S. Provisional application Ser. No. 60/534,045 are incorporated herein. U.S. patent application Ser. No. 13/102,791 is incorporated by reference herein, in its entirety and expressly including any drawings, and is incorporated by reference herein for all purposes.

BACKGROUND OF THE INVENTION

Field of the Invention

This invention generally relates to methods of local and systemic administration of a high-density lipoprotein (HDL) for the prevention, treatment, or amelioration of a vascular disorder, disease or occlusion such as restenosis or vulnerable plaque. The invention also relates HDL coated stents or stents including HDL.

Description of the Background

Cholesterol is a soft, waxy substance found among the lipids (fats) in the bloodstream and in all body's cells. It is an important part of a healthy body because it is used to form cell membranes, some hormones and is needed for other functions. But a high level of cholesterol in the blood—hypercholesterolemia—is a major risk factor for coronary heart disease, which leads to heart attack.

High blood cholesterol is one of the major risk factors for heart disease. A risk factor is a condition that increases one's chance of getting a disease. In fact, the higher one's blood cholesterol level, the greater one's risk for developing heart disease or having a heart attack. Heart disease is the number one killer of women and men in the United States. Each year, more than a million Americans have heart attacks, and about a half million people die from heart disease.

Cholesterol and other fats cannot dissolve in the blood. Cholesterols have to be transported to and from the cells by special carriers called lipoproteins. There are several kinds, but the ones to focus on are low-density lipoprotein (LDL) and high-density lipoprotein (HDL).

Low-density lipoprotein is the major cholesterol carrier in the blood. If too much LDL cholesterol circulates in the blood, it can slowly build up in the walls of the arteries feeding the heart and brain. Together with other substances it can form plaque, a thick, hard deposit that can clog arteries. This condition is known as atherosclerosis. A clot (thrombus) that forms near this plaque can block the blood flow to part of the heart muscle and cause a heart attack. If a clot blocks the blood flow to part of the brain, a stroke results. A high level of LDL cholesterol reflects an increased risk of heart disease. Lower levels of LDL cholesterol reflect a lower risk of heart disease.

About one-third to one-fourth of blood cholesterol is carried by HDL. It has been documented that HDL tends to carry cholesterol away from the arteries and back to the liver, where it is passed from the body or, in the alternative, removes excess cholesterol from plaques and thus slows their growth. A low HDL level indicates a greater risk. A low HDL cholesterol level also may raise stroke risk.

It has been reported the level of serum HDL is inversely associated with the plaque size in coronary arteries (see, for example, von Bergrelen, et al., Circulation 108(22):2757-62 (2003)). U.S. Pat. Nos. 5,746,223 and 6,367,479 to Williams, for example, describe methods for increasing serum HDL level using a composition comprising large unilamellar vesicles or small unilamellar vesicles.

Steven Nissen et al., reported in November 2003 (JAMA 2003; 290: 2292-2300) that in a double-blind, randomized, placebo-controlled multicenter pilot trial, five weeks of infusion of an HDL-mimic, recombinant ApoA-I Milano/phospholipid complex could reduce 4% volume of plaque in patients with prior heart attacks. This study showed systemic delivery of HDL or HDLm may be a promising therapy to reduce plaque.

Nonetheless, there is no report on a method drawn to increase the local level of HDL at the plaque site. Nor is there any report on a method of controlled release of HDL at the plaque site.

The methods and device disclosed herein address the above described problems and needs.

SUMMARY OF THE INVENTION

Provided herein is a method of using an implantable device for controlled release of an apolipoprotein. In some embodiments, the implantable device can be a stent that includes a coating having an apolipoprotein such as HDL, recombinant HDL, HDLm or a combination thereof for release of the apolipoprotein. In some other embodiments, the implantable device can be a bioabsorbable device (e.g., a bioabsorbable stent) that carries or includes the apolipoprotein. The bioabsorbable device can be made of a biocompatible polymer and/or an absorbable metal. The coating or the bioabsorbable device can be capable of providing a controlled release profile, such as fast release, sustained release, intermediate release, or a combination thereof, of the apolipoprotein. The coating or the bioabsorbable device may optionally include a biobeneficial material and/or a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and a combination thereof.

The HDL, recombinant HDL, HDLm and/or optionally one or more additional agents can be coated onto the device free of a polymer or in combination with a biocompatible polymer. The biocompatible polymer can be a hydrophobic polymer, which can be durable or bioabsorbable. The biocompatible polymer also can be a biobeneficial material, a hydrophilic polymer or a polymer having at least one hydrophilic component. The biocompatible polymer also can be a blend of the hydrophobic polymer and the hydrophilic polymer or the polymer having at least one hydrophilic component, optionally with a biobeneficial material.

The implantable device can be used to prevent, treat, inhibit, delay, reduce, or ameliorate a disorder such as vulnerable plaque, restenosis, stenosis, atherosclerosis, thrombosis, hemorrhage, vascular dissection or perforation, vascular aneurysm, chronic total occlusion, claudication, anastomotic proliferation for vein and artificial grafts, bile duct obstruction, ureter obstruction, tumor obstruction, other diseases associated with lipid plaque formation and a combination thereof. The device is preferably useful in patient subsets including type I and type II diabetics, more particularly, where the disorder is restenosis, vulnerable plaque and/or progression of atherosclerosis for type I and type II diabetic patients.

Also provided herein is a method of treating a vascular disorder of a patient, comprising locally administrating HDL, recombinant HDL, HDLm or a combination thereof to a site in need of treatment. In some embodiments, the method is for prevention of lipid plaque formation, reduction in the amount of lipid plaque formed, or delaying the formation of lipid plaque.

DETAILED DESCRIPTION

Provided herein is an implantable device capable of releasing an apolipoprotein. In some embodiments, the implantable device can be, e.g., a stent that includes a coating having an apolipoprotein such as HDL, recombinant HDL, HDLm or a combination thereof for controlled release of the apolipoprotein. In some other embodiments, the implantable device can be a bioabsorbable device (e.g., a bioabsorbable stent) such as that carries or includes the apolipoprotein. The bioabsorbable device can be made of a biocompatible polymer and/or an absorbable metal. Bioabsorbable is intended to include biodegradable, bioerodable, bioresorbable and the like. The coating or the bioabsorbable device is capable of providing a release profile, such as fast release, sustained release, intermediate release, or a combination thereof, of the apolipoprotein. The coating or the bioabsorbable device may optionally include a biobeneficial material and/or a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and a combination thereof.

The HDL, HDLm, recombinant HDL, and/or optionally one or more additional agents can be coated onto the device free of a polymer or in combination with a biocompatible polymer. The biocompatible polymer can be a hydrophobic polymer, which can be durable or bioabsorbable. The biocompatible polymer also can be a biobeneficial material, a hydrophilic polymer or a polymer having at least one hydrophilic component. The biocompatible polymer also can be a blend of the hydrophobic polymer and the hydrophilic polymer or the polymer having at least one hydrophilic component, optionally with a biobeneficial material.

The implantable device can be used to for prevention, treatment, delay, inhibition, reduction, or amelioration (collectively referred to as "treatment" or "treating" unless specifically indicated otherwise) of vascular disease, disorder or occlusion, such as vulnerable plaque, restenosis, stenosis, atherosclerosis, thrombosis, or other disorders and diseases associated with lipid plaque formation. The devices can also be used for the treatment of hemorrhage, vascular dissection or perforation, vascular aneurysm, chronic total occlusion, claudication, anastomotic proliferation for vein and artificial grafts, bile duct obstruction, ureter obstruction, tumor obstruction, and a combination thereof. The device is preferably useful in patient subsets including type I and type II diabetics, more particularly, where the disorder is restenosis, vulnerable plaque and/or progression of atherosclerosis for type I and type II diabetic patients.

As used herein, the term "fast release" refers to a substantial release, e.g., about 50% release of the HDL, recombinant HDL and/or HDLm and/or one or more agents within several minutes to several days, for example, with a period ranging from about 1 hour to about 48 hours, from about 2 hours to about 24 hours or from about 5 hours to about 10 hours.

As used herein, the term "sustained release" refers to a substantial release, e.g., about 50% release of the HDL, recombinant HDL and/or HDLm and/or one or more agents within several days to several years, for example, with a period ranging from about 5 days to about two years, from about 5 days to about 1 year, from about 10 days to 10 months, or from about 1 month to about 6 months.

As used herein, the term "intermediate rate of release" refers to a substantial release, e.g., about 50% release of the HDL, recombinant HDL and/or HDLm and/or one or more agents within several hours to several days, for example, within a period ranging from about 5 hours to about 10 days, from about 5 hours to about 2 days, or from about 10 hours to about 24 hours.

The term "substantial release" refers to a release of about 1% to about 100%, about 5% to about 95%, about 10% to about 90%, about 20% to about 80%, about 30% to about 70%, about 40% to about 60%, or about 50% of the HDL, recombinant HDL and/or HDLm and/or one or more agents.

The term "apolipoprotein" generally refers to any of HDL, recombinant HDL, HDLm and a combination thereof. In some embodiments, the term "apolipoprotein" is used interchangeably with the term "drug".

HDL, Recombinant HDL and HDL Mimics

HDL, or alpha lipoprotein, is a subclass of lipoproteins that transports cholesterol in the blood. HDL is composed of a high proportion of protein and relatively little cholesterol; high levels are associated with decreased risk of coronary heart disease and atherosclerosis. Lipoprotein is a subtype of apolipoproteins, which have a polypeptide moiety and a non-polypeptide moiety. Lipoprotein is a conjugated protein having a lipid component; the principal means for transporting lipids in the blood.

There are two major forms of HDL in the bloodstream of any individual human. One is AI-HDL (or LpA-I), containing the protein apolipoprotein A-I (apoA-I), and the other is AI/AII-HDL (or LpA-I, A-II), containing both apoA-I and the protein apolipoprotein A-II (apoA-II).

The functions of the two components of HDL have been extensively investigated. Studies have shown that there are inverse relationships between HDL-cholesterol and apo A-I plasma levels and the risk of coronary heart disease (CHD). Apo A-II and Lp A-I:A-II plasma levels were found to be related to apo A-II production rate rather than to apo A-II catabolism. HDL reduces CHD risk by promoting the transfer of peripheral free cholesterol to the liver through the so-called "reverse cholesterol transfer" (See, for example, U.S. Pat. Nos. 5,746,223 and 6,367,479 to Williams). Recent studies suggested that apo A-II is not a strong determinant of lipid metabolism, but is rather a modulator of reverse cholesterol transport (see, Tailleux, et al., Atherosclerosis 164(1):1-13 (2002)).

As used herein, in one embodiment, the term HDL encompasses any natural apolipoproteins that include a polypeptide moiety and a non-polypeptide moiety. For example, the apolipoproteins can include apoA-I, apoA-II, AI/AII-HDL, or a mixture thereof that complexes with a non-polypeptide moiety which can be a phospholipid such as cholesterol.

In another embodiment, the HDL can be recombinant apolipoproteins that may include any recombinant apoA-I, apoA-II, AI/AII-HDL, or a mixture thereof that complexes with a non-polypeptide moiety which can be a phospholipid such as cholesterol. The recombinant HDL can be expressed in any organism such as transgenic animal, transgenic plant, or transgenic bacteria. Some representative recombinant HDLs or components thereof are described in, for example, Chiesa, et al., Ann Med. 35(4):267-73 (2003); Hu, et al., Yi Chuan Xue Bao. 30(1):20-4 (2003); Chiesa, Curr Opin Lipidol. 14(2):159-63 (2003); Chroni, et al., J Biol Chem. 28;278(9):6719-30 (2003); Tian, et al., Biochim Biophys Acta. 1599(1-2):56-64 (2002); Gorshkova, et al., Biochemistry 41(33):10529-39 (2002); and Panagotopulos, et al., Protein Expr Purif. 25(2):353-61 (2002)).

Also useful for coating the implantable device described herein are synthetic HDLs or HDL mimics capable of carrying cholesterol away from the arteries and back to the liver. In one embodiment, the term HDLm includes either a synthetic HDL or HDL mimics that has a polypeptide moiety that mimics the structure and/or function of any domain of apoA-I, apoA-II, AI/AII-HDL or a phospholipid moiety. Synthetic HDLs and HDLms are well documented in the art. For example, the HDLm can be ETC-642, which is a complex of a 22-amino acid peptide and phospholipids that mimics the functions of HDL. The peptide component of ETC-642 mimics the biological properties of apolipoproteinA-I, the major protein in HDL, to promote removal of excess cholesterol and other lipids from artery walls and other tissues and enhance reverse lipid transport (See, for example, "Single-dose Intravenous Infusion of ETC-642, a 22-mer ApoA-I Analogue and Phospholipids Complex, Elevates HDL-C in Atherosclerosis Patients," American Heart Association Scientific Sessions, Nov. 11, 2003, Orlando, Fla.). Other useful HDLms are cholesterol acceptor compounds such as large unilamellar vesicles or small unilamellar vesicles described in, for example, U.S. Pat. Nos. 5,746,223, 5,858,400; 5,948,435; 6,079,416 and 6,367,479 to Williams. Other representative useful HDLms may also include Apo A-I and/or Apo A-II agonists or modulators described in U.S. Pat. Nos. 6,602,854; 6,585,995; 6,573,239; 6,518,412; 6,376,464; 6,265,377; 6,156,727; 6,046,166; and 6,037,323.

In one embodiment, an implantable device such as a stent can be coated with a coating that includes HDL, recombinant HDL, HDLm, or a combination thereof to delivery any of these apolipoprotein species. Implanted stents have been used to carry medicinal agents, such as thrombolytic agents. U.S. Pat. No. 5,163,952 to Froix discloses a thermal memoried expanding plastic stent device formulated to carry a medicinal agent in the material of the stent itself. Pinchuk, in U.S. Pat. No. 5,092,877, discloses a stent of a polymeric material which may have a coating associated with the delivery of drugs. Other patents which are directed to devices of the class utilizing bio-degradable or bio-sorbable polymers include Tang et al., U.S. Pat. No. 4,916,193, and MacGregor, U.S. Pat. No. 4,994,071.

The coating may optionally include one or more additional bioactive agent such as a phospholipid. The phospholipid includes, for example, phosphoryl choline, phosphoryl serine, phosphoryl inositol, di-phosphoryl glycerol, zwitterions ion phosphoryl ethanolamine, etc, and a combination thereof. The composition can be used to form a coating on an implantable device such as a drug-delivery stent.

In a further aspect of the present invention, any of the apolipoproteins can be carried or included in a durable, biodegradable or bioabsorbable medical device, e.g., a stent.

In another embodiment, HDL, recombinant HDL, and HDLm can be delivered locally without a polymer carrier, such as through an implantable pump or through coating the apolipoprotein directly on the implantable devices such as a stent. Implantable pump has been successfully used in controlled, local delivery of diagnostic and therapeutic agents (see, e.g., Perry, C. R., et al., Clin Orthop. 226:222-30 (1988); Bret Berner, Steven M. Dinh, Electronically Controlled Drug Delivery, CRC Press, 1998).

Coating Constructs

The HDL, recombinant HDL, HDLm, and optionally one or more additional bioactive agents other than HDL, recombinant HDL, and HDLm, and any of the polymers described herein can be made into different coating constructs to provide various release profile of the HDL, recombinant HDL and/or HDLm and optionally one or more bioactive agents other than the HDL and HDLm.

In one aspect of the present invention, the coating construct comprises a layer of the HDL, recombinant HDL and/or HDLm and optionally one or more bioactive agents and a topcoat comprising a polymer or polymer blend. The polymer can be a hydrophobic biocompatible polymer, a hydrophilic biocompatible polymer, or a biocompatible polymer that includes a hydrophilic component. The hydrophilic polymer topcoat can be a bioresorbable or a durable hydrogel or a biocompatible_coating defined herein. In a further embodiment, the polymer is a blend of any of the hydrophobic biocompatible polymer, hydrophilic biocompatible polymer or the biocompatible polymer that includes a hydrophilic component.

In some embodiments, the coating construct comprises a polymeric reservoir layer that includes the HDL, recombinant HDL and/or HDLm and optionally one or more bioactive agents. The polymer can be a hydrophobic biocompatible polymer, a hydrophilic biocompatible polymer, or a biocompatible polymer that includes a hydrophilic component. In a further embodiment, the polymer is a blend of any of the hydrophobic biocompatible polymer, hydrophilic biocompatible polymer or the biocompatible polymer that includes a hydrophilic component.

In a further aspect of the present invention, the coating construct comprises two or more reservoir layers that include the HDL, recombinant HDL and/or HDLm and optionally one or more bioactive agents, and a polymer or a polymer blend. The polymer can be a hydrophobic biocompatible polymer, a hydrophilic biocompatible polymer, or a biocompatible polymer that includes a hydrophilic component. In a further embodiment, the polymer is a blend of any of the hydrophobic biocompatible polymer, hydrophilic biocompatible polymer or the biocompatible polymer that includes a hydrophilic component.

The coating construct can be multiple layers, such as a primer layer, a reservoir layer including the drug(s) and a topcoat layer. The reservoir layer can include sublayers of the same drug or different drugs. The reservoir layer can be with or without polymer(s).

The coating constructs described herein can provide a controlled release of the HDL, recombinant HDL and/or HDLm and optionally one or more bioactive agents. When a fast release of the HDL, recombinant HDL and/or HDLm and/or one or more agents is desirable, a hydrophilic biocompatible or a biocompatible polymer including a hydrophilic component can be used to form a reservoir layer with relatively high drug-to-polymer ratio or a topcoat layer. Alternatively, the bioactive agents can be applied directly on the device without carrier polymer with or without a topcoat polymer. When a sustained release of the HDL, recombinant HDL and/or HDLm and/or one or more agents is desirable, a relatively hydrophobic biocompatible polymer can be used to form a reservoir layer or a topcoat layer. Alternatively a hydrophilic polymer can be used with relatively low drug-to-polymer ratio. When a bioresorbable polymer is used as a carrier, the drug release could be two phases, with a first phase of drug release through diffusion via percolation channel and with the second phase of drug release through polymer degradation and drug dissolution. If an intermediate release rate of the HDL, recombinant HDL and/or HDLm and/or one or more agents is desirable, a polymer blend of any of the hydrophobic biocompatible polymer, hydrophilic biocompatible polymer or the biocompatible polymer that includes a hydrophilic component can be used. The ratio of the hydrophilic polymer and/or the polymer containing a hydrophilic component to the hydrophobic biocompatible polymer can be varied to achieve a desired rate of release. If apolipoprotein is lipophilic, the drug can be applied directly on the device with or without a durable or bioresorbable polymer topcoat to achieve intermediate release profile. A coating construct with multiple drug reservoir layers can be used to achieve a combination of a fast release with a sustained release of the HDL, recombinant HDL and/or HDLm and/or one or more agents.

In one embodiment, the device includes a coating that comprises a HDL, recombinant HDL and/or HDLm and a hydrophobic biocompatible polymer. The biocompatible polymer can provide a controlled release of a bioactive agent, if included in the coating and/or if bound to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, poly(lactic acid) (PLA) based drug delivery systems have provided controlled release of many therapeutic drugs with various degrees of success (see, for example, U.S. Pat. No. 5,861,387 to Labrie, et al.). The release rate of the bioactive agent can be controlled by, for example, selection of a particular type of biocompatible polymer, which can provide a desired release profile of the bioactive agent. The release profile of the bioactive agent can be further controlled by selecting the molecular weight of the biocompatible polymer, the ratio of the biocompatible polymer to the bioactive agent, and the degradation rate of bioresorbable polymer carrier and/or topcoat. Additional ways to control the release of the bioactive agent are, for example, specific design of the polymer coating construct, conjugating the active agent onto the polymeric backbone, designing a micro-phase separated polymer that includes rigid and mobile segments where the active resides in the more mobile segment, and designing a polymer in which the bioactive has an appropriate level of solubility. One of ordinary skill in the art can readily select a carrier system using a biocompatible polymer to provide a controlled release of the bioactive agent. Examples of the controlled release carrier system can come from the examples provided above; however, other possibilities not provided are also achievable.

In some embodiments, the device provides a controlled or sustained release of the HDL, recombinant HDL and/or HDLm over a period ranging from, for example, several days to several months or years.

Biocompatible Polymers

The biocompatible polymer that can be used with the HDL, recombinant HDL or HDLm in the coatings or medical devices described herein can be any biocompatible polymer known in the art, which can be biodegradable or nondegradable and can be hydrophobic or hydrophilic. Representative examples of polymers that can be used to coat an implantable device in accordance with the present invention include, but are not limited to, poly(ester amide), ethylene vinyl alcohol copolymer (commonly known by the generic name EVOH or by the trade name EVAL), poly (hydroxyvalerate), poly(L-lactic acid), poly(L-lactide), poly (D,L-lactide), poly(L-lactide-co-D,L-lactide), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(D,L-lactide-co-glycolide) (PDLLAGA), poly(glycolic acid-co-trimethylene carbonate), polyphosphoester, polyphosphoester urethane, poly(amino acids), polycyanoacrylates, poly(trimethylene carbonate), poly(iminocarbonate), poly(butylene terephthalate-co-poly((ethylene glycol) (PEG)-terephthalate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides such as vinylidene fluoride based homo or copolymer under the trade name Solef™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics such as polystyrene, polyvinyl esters, such as polyvinyl acetate, copolymers of vinyl monomers with each other and olefins such as ethylene-methyl methacrylate copolymers, acrylonitrile-styrene copolymers, ABS resins, and ethylene-vinyl acetate copolymers, polyamides such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

A preferred biocompatible, hydrophobic polymer is a polyester, such as one of poly(D,L-lactic acid) (PDLLA), poly(L-lactic acid) (PLLA), poly(D-lactic acid) (PDLA), poly(D,L-lactic acid-co-glycolic acid) (PDLLGA), poly (glycolic acid) (PGA), polyhydroxyalkanoates (PHA), poly (3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), polycaprolactone (PCL), and a combination thereof.

The biobeneficial material that can be used with the HDL or HDLm to form the coatings or medical devices described herein can be a polymeric material or non-polymeric material. The biobeneficial material is preferably flexible and biocompatible and/or biodegradable (a term which includes bioerodable, biodegradable and bioabsorbable), more preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and a combination thereof. In some embodiments, the polymer can exclude any one of the aforementioned polymers.

In a preferred embodiment, the biobeneficial material is a block copolymer having flexible poly(ethylene glycol) and poly(butylene terephthalate) blocks (PEGT/PBT) (e.g., PolyActive™). PolyActive™ is intended to include AB, ABA, BAB copolymers having such segments of PEG and PBT (e.g., poly(ethylene glycol)-block-poly(butylene-terephthalate)-block poly(ethylene glycol) (PEG-PBT-PEG).

Representative hydrophilic materials that can be used include hyaluronate, heparin, polyethylene glycol, polyalkene oxides, block copolymer poly(ethylene glycol terephtalate)/poly(butylene terephtalate) (PEGT/PBT) (PolyActive™), phosphoryl choline, poly(aspirin), poly (N-vinylpyrrolidone) (PNVP), SIS-PEG, polystyrene-PEG, polyisobutylene-PEG, PCL-PEG, PLA-PEG, PMMA-PEG, PDMS-PEG, PVDF-PEG, SIS-hyaluronic acid (HA), poly-styrene-HA, polyisobutylene-HA, PCL-HA, PLA-HA, PMMA-HA, PVDF-HA, SIS-heparin, polystyrene-heparin, polyisobutylene-heparin, PCL-heparin, PLA-heparin, PMMA-heparin, PVDF-heparin, and a combination thereof.

Bioactive Agents

Bioactive agents that can be used with HDL, recombinant HDL, and/or HDLm can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the agent required to produce a favorable therapeutic effect should be less than the level at which the agent produces toxic effects and greater than the level at which non-therapeutic results are obtained. The dosage or concentration of the agent required can depend upon factors such as the particular circumstances of the patient, the nature of the tissues being delivered to, the nature of the therapy desired, the time over which the ingredient administered resides at the vascular site, and if other agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, endocardial leads (e.g., FINELINE® and ENDOTAK ®, available from Guidant Corporation, Santa Clara, Calif.), and implantable pump. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or a combination thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In some embodiments, a bioabsorbable or bioerodable stent is used to carry HDL, recombinant HDL or HDLm.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is particularly useful for treating occluded regions of blood vessels caused by atherosclerosis, abnormal or inappropriate migration and proliferation of smooth muscle cells, thrombosis, and restenosis. Stents may be placed in a wide array of blood vessels, both arteries and veins.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

Embodiments of Alternative Methods of Treatment

As indicated before, HDL, recombinant HDL, HDLm and optionally one or more agents can be delivered locally by means other than a stent. In some embodiments, delivery can be systemic. The therapy can be exclusively a non-stent therapy. In some embodiments, HDL, recombinant HDL or HDLm can be delivered locally and/or systemically, in conjunction with stent therapy. The stent can be a bare metal stent, a drug delivery stent, or a bioabsorbable stent. Local or systemic delivery can be before, during and/or subsequent to the implantation of the stent. In some embodiments, a drug eluting stent can be implanted (for example carrying everolimus, ABT-578™, paclitaxel, docetaxel, paclitaxel derivatives, or rapamycin) and prior to, during and/or subsequent to the implantation of the drug eluting stent, HDL, recombinant HDL or HDLm can be delivered via a catheter or a porous balloon system. Drug delivery via catheters or balloon systems is known to one having ordinary skill in the art.

For various modes of local or systemic delivery, HDL, recombinant HDL or HDLm can be formulated with a pharmaceutical carrier of solid or liquid form. A solid carrier can include one or more substances which may act as flavoring agents, lubricants, solubilizers, suspending agents, fillers, glidants, compression aids, binders or tablet-disintegrating agents. Additionally, the solid carrier can be an encapsulating material. In powder, the carrier can be a finely divided solid. In tablets, HDL, recombinant HDL or HDLm (and optionally one or more additional agents) is mixed with a carrier having the necessary compression properties in suitable proportions and compacted in the shape and size desired. The powder and tablets can contain up to about 99% of the active component. Suitable solid carriers include, for example, calcium phosphate, magnesium stearate, talc, sugars, lactose, dexyin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. HDL, recombinant HDL or HDLm (and optionally one or more additional agents) can be dissolved or suspended in a pharmaceutically acceptable liquid carrier such as water or suitable organic solvents. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carrier for oral and parenteral administration include water, sucrose solution, lipid formulations, phosphate buffered saline solution, alcohols such as monohydric and polyhydric alcohols, and emulsions such as the oil-in-water or water-in-oil type. For parenteral administration, the carrier can also be an oily ester such as ethyl oleate and isopropyl myristate. The liquid carrier for pressurized compositions can be, for example, a halogenated hydrocarbon.

In some embodiments, systemic administration of HDL, recombinant HDL or HDLm (and optionally one or more additional agents) can be accomplished orally or parenterally including intravascularly, rectally, intranasally, intrabronchially, or transdermally. Liquid carriers which are sterile solutions or suspensions can be injected intramuscularly, intraperitoneally, subcutaneously, and intravenously. Rectal administration can be in the form of conventional suppository. For administration by intranasal or intrabronchial inhalation or insufflation, HDL, recombinant HDL or HDLm (and optionally one or more additional agents) can be formulated into an aqueous or partially aqueous solution, which can then be utilized in the form of an aerosol. HDL, recombinant HDL or HDLm (and optionally one or more additional agents) can be administered transdermally through the use of a transdermal patch and a carrier that is inert to and mutually compatible with the active component)s), is non-toxic to the skin, and allows for the delivery of the active component(s) for systemic absorption into the blood stream via the skin. Again, this treatment can be conjunction with stent therapy. The treatment can be initiated in advance of stent implantation, generally simultaneously or subsequent to the stent being implanted in the body. The carrier may take any number of forms such as creams, ointments, pastes, and gels. The creams and ointments may be viscous liquids or semisolid emulsions of either the oil-in-water or water-in-oil type. Pastes made of absorptive powders dispersed in petroleum or hydrophilic petroleum containing the active component may also be suitable. Other devices capable of releasing HDL, recombinant HDL or HDLm (and optionally one or more additional agents) into the blood stream include semi-permeable membranes covering a reservoir containing the active component, with or without a carrier.

In some embodiments, local administration can be accomplished by a variety of techniques which administer HDL, recombinant HDL or HDLm (and optionally one or more additional agents) at or near the target site. The following examples of local delivery techniques are provided for illustrative purposes and are not intended to be limiting. Examples include local delivery catheters, site specific carriers, non-stent implants, direct application, or direct injection. Local delivery by a catheter allows for the administration directly to a targeted lesion. Local delivery by site specific carriers is conducted by attaching HDL, recombinant HDL or HDLm to a carrier which will direct or link the drug to targeted cells. Examples of this delivery technique include the use of carrier such as a protein ligand, a monoclonal antibody or a membrane anchored linker.

Local delivery by a non-stent implant is the placement of a matrix carrying HDL, recombinant HDL or HDLm (optionally with other drugs) at the target site. The matrix can release HDL, recombinant HDL or HDLm component via, for example, diffusion, degradation, chemical reaction, solvent activators, etc. One example of local delivery by an implant can include direct injection of vesicles or micro-particles into the target site. These micro-particles may be composed of substances such as proteins, lipids, carbohydrates or synthetic polymers. The micro-particles can have HDL, recombinant HDL or HDLm impregnated therein and/or coated thereon.

Yet in another example, a delivery system is provided in which a polymer that contains HDL, recombinant HDL or HDLm (and optionally other agents) is injected into the lesion in liquid form. The polymer can then be cured to form the implant in situ. In situ polymerization can be accomplished by photocuring or chemical reaction. Photocuring is conducted by mixing a polymer such as, but not limited to, acrylate or diacrylate modified polyethylene glycol (PEG), PLURONIC®, polybutylene teraphthalate-co-polyethylene oxide, polyvinyl alcohol, hydroxy ethyl methacrylate (HEMA), hydroxy ethyl methacrylate-co-polyvinyl pyrrolidone, HEMA-co-PEG, or glycidol acrylate modified Heparin or sulfated dextran with the active component, with or without a photosensitizer (e.g., benzophenone) or a photoinitiator (e.g., 2,2 dimethoxy 2-phenyl acetophenone, and eosin-Y). The precursor system can be activated by a suitable wavelength of light corresponding to the system. The activation will result in a cured system that incorporates HDL, recombinant HDL or HDLm. Chemical reaction can be conducted by incorporating di-isocyanate, aldehyde, N-hydroxy succinimide, di-imidazole, —NH2, —COOH, with a polymer such as PEG or HEMA. The process of photocuring and chemical reaction is known to one of ordinary skill in the art.

Application via implants is not limited to the above described routes and other techniques such as grafts, micropumps or application of a fibrin glue or hydrogel containing HDL, recombinant HDL or HDLm around the exterior of a designated region of the adventitia can also be implemented by one of ordinary skill in the art.

In some embodiments, local delivery by direct application includes the use of topical applications. An example of a local delivery by direct application is applying the HDL, recombinant HDL or HDLm (optionally with other agents) directly to the arterial bypass graft during the surgical procedure. Another example of local delivery by direct application includes delivery of the HDL, recombinant HDL or HDLm into the pericardial sac as is known by one of ordinary skill in the art.

Local delivery by direct injection includes injecting a liquid carrier containing HDL, recombinant HDL or HDLm (optionally with other agents) directly into the proliferative or target site. The liquid carrier should be inert to and mutually compatible with HDL, recombinant HDL or HDLm. The component can be in true solution or suspended in fine particles in the carrier. A suitable example of an inert carrier includes a sterile saline solution.

Systemic or local administration via the various disclosed routes may be continuous, intermittent, applied in a single treatment or multiple treatments. For example a regiment can be contemplated which involves a single dose given before and/or at the time of the treatment procedure, e.g., balloon or stent therapy, and with a follow-up dose delivered after a predetermined time period subsequent to the treatment procedure.

One of the aforementioned bioactive or therapeutic agents, e.g., everolimus,-ABT-578™, paclitaxel, docetaxel, paclitaxel derivatives, or rapamycin can also be administrated prior to, contemporaneously with, or subsequent to the administration of HDL, recombinant HDL or HDLm. This can be accomplished via the same route or via mixed routes. For example, a vascular stent can be impregnated with everolimus and HDL, recombinant HDL or HDLm can be administered orally o prior to the implantation procedure and/or contemporaneously via a catheter.

Local, including via a stent, and systemic application of HDL, recombinant HDL or HDLm is particularly useful for prevention, treatment, delay, inhibition, reduction, or amelioration (collectively referred to as "treatment" or "treating" unless specifically indicated otherwise) of vascular disease, disorder or occlusion, such as vulnerable plaque, restenosis, stenosis, atherosclerosis, thrombosis, as well as other disorders associated with lipid plaque formation. In some embodiments, local (e.g., via stent) and systemic application is for prevention of lipid plaque formation, reduction in the amount of lipid plaque formed, or delaying the formation of lipid plaque.

The embodiments of the invention are also useful for hemorrhage, vascular dissection or perforation, vascular aneurysm, chronic total occlusion, claudication, anastomotic proliferation for vein and artificial grafts, bile duct obstruction, ureter obstruction, tumor obstruction, and a combination thereof.

The device is preferably useful in patient subsets including type I and type II diabetics, more particularly, where the disorder is restenosis, vulnerable plaque and/or progression of atherosclerosis for type I and type II diabetic patients.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:
   poly(3-hydroxyhexanoate), poly(4-hydroxyhexanoate), or a combination thereof; and
   a high-density lipoprotein (HDL), a recombinant HDL, a high-density lipoprotein mimic (HDLm), or a combination thereof;
   wherein the HDLm comprises a polypeptide moiety that mimics the structure of a domain of apoA-I, apoA-II, or AI/AII-HDL.

2. The stent of claim 1, wherein the stent is a bioabsorbable polymeric stent.

3. The stent of claim 2, wherein the high-density lipoprotein (HDL), the recombinant HDL, the high-density lipoprotein mimic (HDLm), or the combination thereof is incorporated in the body of the stent.

4. The stent of claim 2, wherein the stent comprises a polymeric coating and the high-density lipoprotein (HDL), the recombinant HDL, the high-density lipoprotein mimic (HDLm), or the combination thereof is incorporated in the coating.

5. The stent of claim 1, wherein the stent comprises a polymeric coating comprising a polymer, the polymer comprising one or more hydrophobic biocompatible polymers, one or more hydrophilic biocompatible polymers, one or more biocompatible polymers having at least one hydrophilic component, or a combination thereof such that the high-density lipoprotein (HDL), the recombinant HDL, the high-density lipoprotein mimic (HDLm), or the combination thereof is incorporated in the coating.

6. The stent of claim 1, wherein the stent comprises a coating, the coating comprising one or more reservoir regions, at least one reservoir region comprising the high-density lipoprotein (HDL), the recombinant HDL, the high-density lipoprotein mimic (HDLm), or the combination thereof incorporated therein, and a topcoat region over the at least one reservoir region.

7. The stent of claim 6, wherein the coating additionally comprises a primer region beneath the reservoir region(s).

8. The stent of claim 1, wherein the stent additionally comprises one or more drugs.

9. The stent of claim 8, wherein at least one of the one or more drugs is everolimus, zotarolimus, paclitaxel, docetaxel, rapamycin, or a combination thereof.

10. The stent of claim 1, wherein the stent further comprises a biobeneficial material, and the biobeneficial material comprises one or more polyethers; poly(ethylene glycol); one or more copoly(ether-esters); PEO/PLA; one or more polyalkylene oxides; poly(ethylene oxide); poly(propylene oxide); one or more poly(ether esters); one or more polyalkylene oxalates; one or more polyphosphazenes; phosphorylcholine; choline; poly(aspirin); poly(styrene-isoprene-styrene)-PEG (SIS-PEG); polystyrene-PEG; polyisobutylene-PEG; polycaprolactone-PEG (PCL-PEG); PLA-PEG; poly(methyl methacrylate)-PEG (PMMA-PEG); polydimethylsiloxane-co-PEG (PDMS-PEG); poly(vinylidene fluoride)-PEG (PVDF-PEG); one or more polypropylene oxide-co-polyethylene glycol surfactants; one or more poly(ethylene glycol)-block-poly(butyleneterephthalate)-block-poly(ethylene glycol) polymers; poly(tetramethylene glycol); one or more biomolecules; fibrin; fibrinogen; cellulose; starch; collagen; dextran; dextrin; hyaluronic acid; one or more fragments of hyaluronic acid; heparin; one or more fragments of heparin; glycosaminoglycan (GAG); one or more polysaccharides; elastin; chitosan; alginate; one or more silicones; or a combination thereof.

11. A method of treating a patient suffering from one or more medical conditions comprising implanting a stent in the patient, the stent comprising:
    poly(3-hydroxyhexanoate), poly(4-hydroxyhexanoate), or a combination thereof; and
    a high-density lipoprotein (HDL), a recombinant HDL, a high-density lipoprotein mimic (HDLm), or a combination thereof;
    wherein the HDLm comprises a polypeptide moiety that mimics the structure of a domain of apoA-I, apoA-II, or AI/AII-HDL; and
    wherein at least one of the medical conditions is vulnerable plaque, restenosis, stenosis, atherosclerosis, thrombosis, hemorrhage, vascular dissection or perforation, vascular aneurysm, claudication, anastomotic proliferation for vein and artificial grafts, or a combination thereof.

12. The method of claim 11, wherein the method additionally comprises local administration of a high-density lipoprotein (HDL), a recombinant HDL, a high-density lipoprotein mimic (HDLm), or a combination thereof.

13. The method of claim 12, wherein the local administration is delivery by a catheter, a porous balloon, or both.

14. The method of claim 12, wherein local administration is delivery by an implantable pump, an implant which is not a stent, direct injection, local topical administration, or a combination thereof.

15. The method of claim 11, wherein the patient is a type I diabetic or a type II diabetic.

16. The method of claim 11, wherein the stent is a bioabsorbable polymeric stent.

17. The method of claim 16, wherein the high-density lipoprotein (HDL), the recombinant HDL, the high-density lipoprotein mimic (HDLm), or the combination thereof is incorporated in the body of the stent.

18. The method of claim 16, wherein the stent comprises a polymeric coating and the high-density lipoprotein (HDL), the recombinant HDL, the high-density lipoprotein mimic (HDLm), or the combination thereof is incorporated in the coating.

19. The method of claim 11, wherein the stent comprises a polymeric coating comprising a polymer, the polymer comprising one or more hydrophobic biocompatible polymers, one or more hydrophilic biocompatible polymers, one or more biocompatible polymers having at least one hydrophilic component, or a combination thereof such that the high-density lipoprotein (HDL), the recombinant HDL, the high-density lipoprotein mimic (HDLm), or the combination thereof is incorporated in the coating.

20. The method of claim 11, wherein the stent comprises a coating, the coating comprising one or more reservoir regions, at least one reservoir region having the high-density lipoprotein (HDL), the recombinant HDL, the high-density lipoprotein mimic (HDLm), or the combination thereof incorporated therein, and a topcoat region over the at least one reservoir region.

21. The method of claim 20, wherein the coating additionally comprises a primer region beneath the reservoir region(s).

22. The method of claim 11, wherein the stent additionally comprises one or more drugs.

23. The method of claim 22, wherein at least one of the one or more drugs is everolimus, zotarolimus, paclitaxel, docetaxel, rapamycin, or a combination thereof.

* * * * *